United States Patent [19]

Chen et al.

[11] Patent Number: 5,273,979

[45] Date of Patent: * Dec. 28, 1993

[54] C-31 DESMETHYL FR-900520 CYCLIC HEMIKETAL IMMUNOSUPPRESSANT AGENT

[75] Inventors: Shieh-Shung T. Chen, Morganville; Raymond F. White, Englishtown; Georgette Dezeny, Short Hills; Byron H. Arison, Watchung; Thomas R. Beattie, Scotch Plains; Amy M. Hale, Glen Gardner; Francis Dumont, Rahway, all of N.J.

[73] Assignee: Merck & Co., Inc., Rahway, N.J.

[*] Notice: The portion of the term of this patent subsequent to Sep. 22, 2009 has been disclaimed.

[21] Appl. No.: 738,997

[22] Filed: Aug. 1, 1991

[51] Int. Cl.$^5$ .................. A61K 31/395; C07D 491/16
[52] U.S. Cl. ...................................... 514/291; 540/456; 514/183
[58] Field of Search ........................ 540/456; 514/291

[56] References Cited

U.S. PATENT DOCUMENTS 3,244,592  4/1966  Arai ..................... 540/455

FOREIGN PATENT DOCUMENTS

| 0184162 | 6/1986 | European Pat. Off. | 540/456 |
| 0349049 | 1/1990 | European Pat. Off. | 540/456 |
| 0349061 | 1/1990 | European Pat. Off. | 540/456 |
| 0388152 | 9/1990 | European Pat. Off. | 540/456 |
| 0388153 | 9/1990 | European Pat. Off. | 540/456 |
| WO89/05304 | 6/1989 | PCT Int'l Appl. . | |

OTHER PUBLICATIONS

J. Antibiotics A15, pp. 231-232, by Arai (1962).

*Primary Examiner*—Robert T. Bond
*Attorney, Agent, or Firm*—Charles M. Caruso; J. Eric Thies

[57] ABSTRACT

Described is a process for producing a new immunosuppressant, a C-31 desmethyl, C-19/C-22 cyclic hemiketal biotransformation analog (Compound I) of FR-900520, under novel fermentation conditions utilizing the novel microorganism, *Streptomyces, lavendulae* ATCC No. 55209. Also disclosed is the C-31 methylated derivative (Compound II) of Compound I produced by enzymatic methylation using 31-O-desmethylimmunomycin O-methyl transferase, (DIMT), a methyl transferase enzyme. The macrolide immunosuppressants are useful in preventing human host rejection of foreign organ transplants, e.g. bone marrow, liver, lung, kidney and heart transplants.

2 Claims, 6 Drawing Sheets

C-31 DESMETHYL FR-900520 CYCLIC HEMIKETAL IMMUNOSUPPRESSANT AGENT

BACKGROUND OF THE INVENTION

1. Field of the Invention

This invention relates to a new FK-506 type immunosuppressant agent, a C-31 desmethyl, C-19/C-22 cyclic hemiketal analog of FR-900520 (FK-520), Compound I, a novel fermentation process for its production, utilizing the novel microorganism Streptomyces lavendulae ATCC No. 55209. The process involves culturing the microorganism in the presence of FR-900520 under conditions which induce C-31 demethylation and C-19/C-22 cyclic hemiketal formation of FR-900520. Also disclosed is the C-31 methylated derivative of Compound I, designated as Compound II, produced by enzymatic methylation of Compound I using DIMT, a methyl transferase enzyme. Also disclosed is a method of its use in a human host for treatment of autoimmune diseases, infectious diseases and/or prevention of organ transplant rejections.

2. Brief Description of Disclosures in the Art

In 1983, the U.S. FDA approved cyclosporin, and extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide immunosuppressant FK-506 which is reputed to be 100 times more effective than cyclosporin. The macrolide is produced by fermentation of a particular strain of Streptomyces tsukubaensis. Also described is the closely related macrolide immunosuppressant FR-900520, produced by S. hygroscopicus subsp. yakushimaensis. The terms "FK-520" and "immunomycin" also used by Merck & Co. Inc. as synonyms for FR-900520.

U.S. Pat. No. 3,244,592 to T. Arai describes the culturing of Streptomyces hygroscopicus var. ascomyceticus to produce the antifungal "ascomycin", which has been shown to be the same compound as FR-900520.

There is, however, no description in the literature of the production of any FK-506 type immunosuppressive agents, which substantially lack the side effects or similar side effects to cyclosporin.

In this regard, new FK-506 type immunosuppressants are continuously being searched for.

SUMMARY OF THE INVENTION

It has been found that a new FK-506 immunosuppressant, Compound I, can be obtained by the fermentation of the microorganism Streptomyces lavendulae ATCC No. 55209, together with the macrolide immunosuppressant FR-900520, under submerged aerobic conditions in an aqueous carbohydrate medium, containing a nitrogen nutrient, said conditions being conducted at a pH of about 7, which are sufficient to C-31 demethylate FR-900520 and induce C-19/C-22 cyclic hemiketal formation.

The resultant Compound I exhibits FK-506 immunosuppressant activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay".

The principle of this assay, as described in J. Immunology, Vol. 144, pp. 251-258 (1990) by F. Dumont et al, is to measure the proliferation of mouse T lymphocytes stimulated with the combination of ionomycin plus PMA. A positive sample e.g. FK-506, in this assay will inhibit T-cell proliferation, as indicated by reduced tritiated thymidine uptake.

Also disclosed is the C-31 methylated analog of Compound I, designated as Compound II, produced by enzymatic methylation of Compound I by DIMT, a methyl transferase enzyme.

In accordance with this invention, there is provided a process for producing a new FK-506 immunosuppressant, identified as Compound I, comprising the step of culturing a strain of Streptomyces lavendulae, ATCC No. 55209, together with FR-900520 under submerged aerobic fermentation conditions in an aqueous carbohydrate medium, containing a nitrogen nutrient, for a sufficient time to produce product Compound I.

Figure 1A:
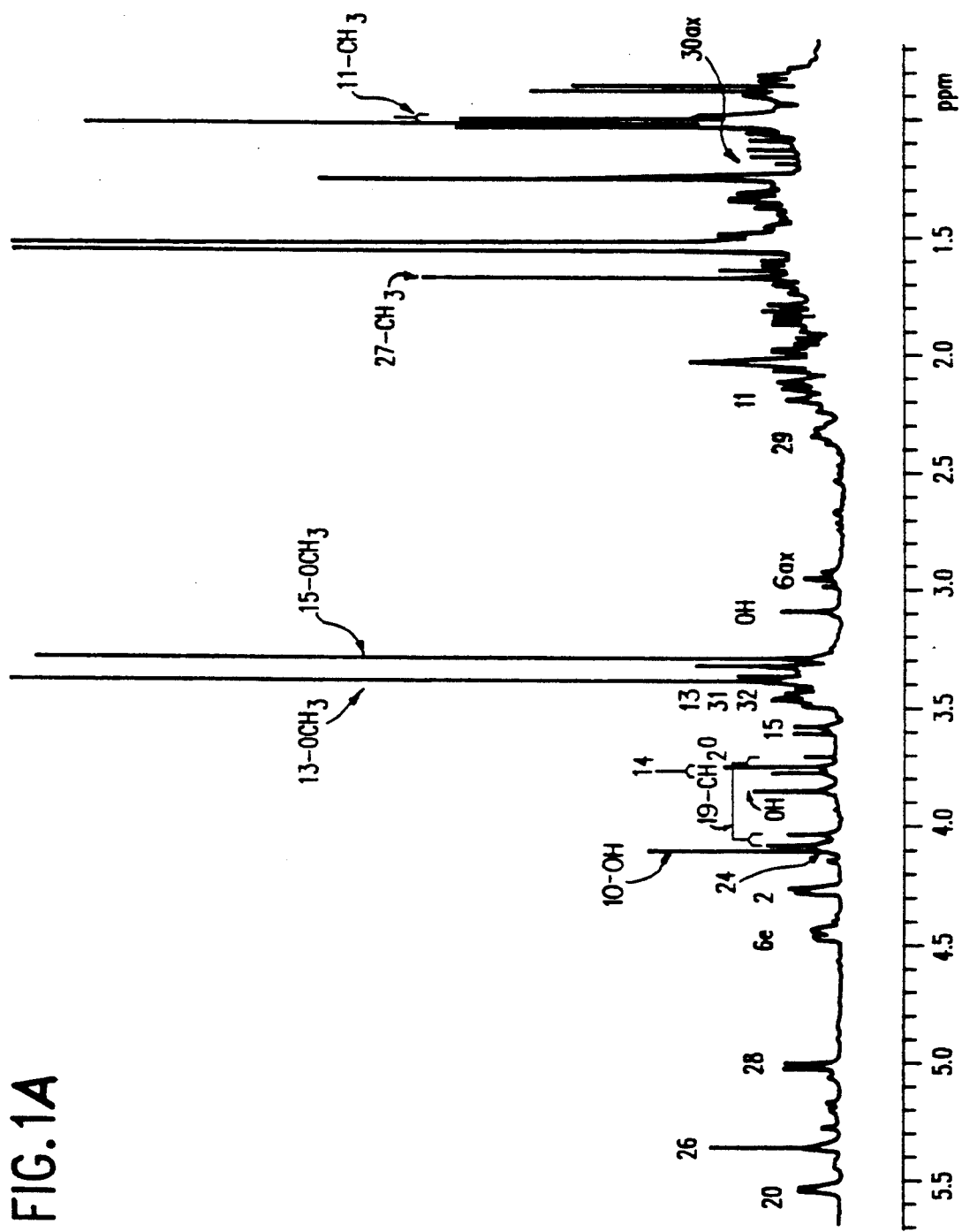
FIG. 1A is an $^1$H nuclear magnetic resonance (NMR) spectrum taken at 400 MHz of Compound I in CDCl$_3$.
Figure 1B:
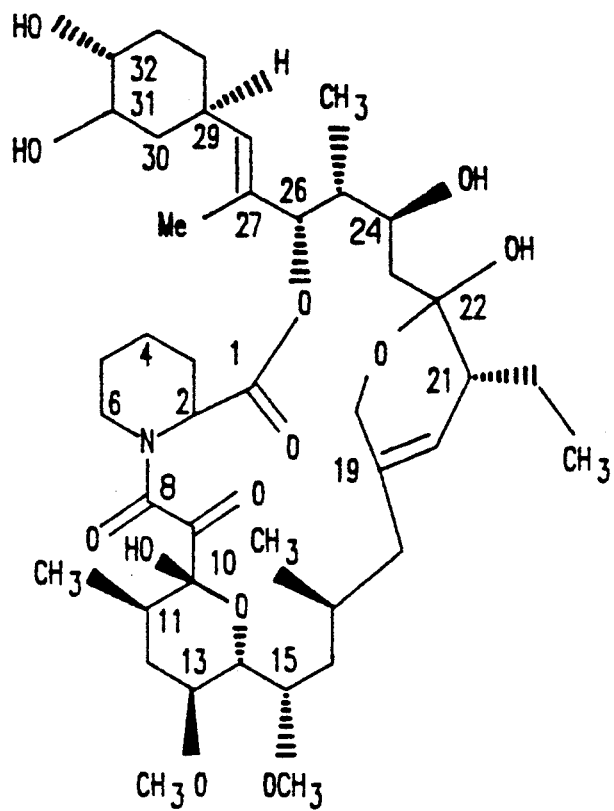
FIG. 1B illustrates the assigned molecular structure.

Further provided is a new FK-506 immunosuppressant, Compound I, produced by the above process which exhibits positive inhibition of T-cell activation by the T-cell proliferation assay and exhibits a proton nuclear magnetic resonance spectrum illustrated in FIG. 1 and has an assigned structure as also identified in FIG. 1.

Also provided is a pharmaceutical composition containing a therapeutically effective amount of Compound I in combination with a pharmaceutically acceptable, substantially non-toxic carrier or excipient.

Figure 2A:
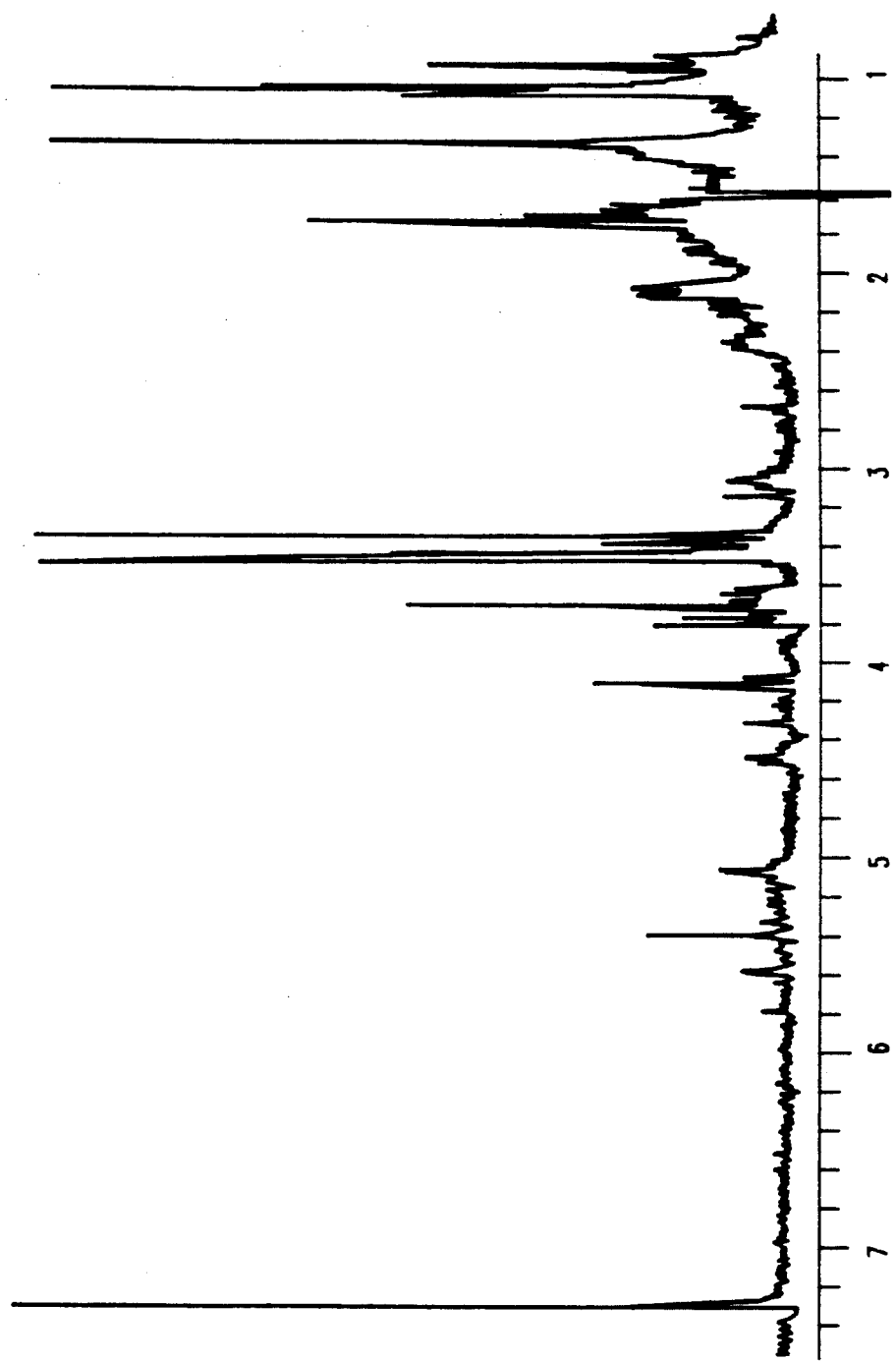
FIG. 2A is an $^1$H MR spectrum taken at 400 MHz of Compound II in CDCl$_3$ solution and FIG. 2B illustrates the assigned molecular structure.
Figure 2B:
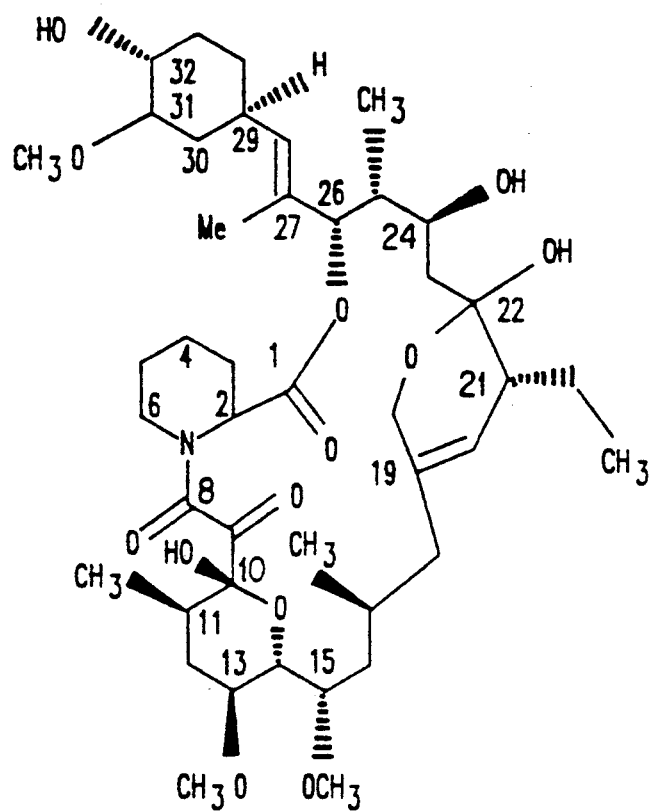
Figure 3A:
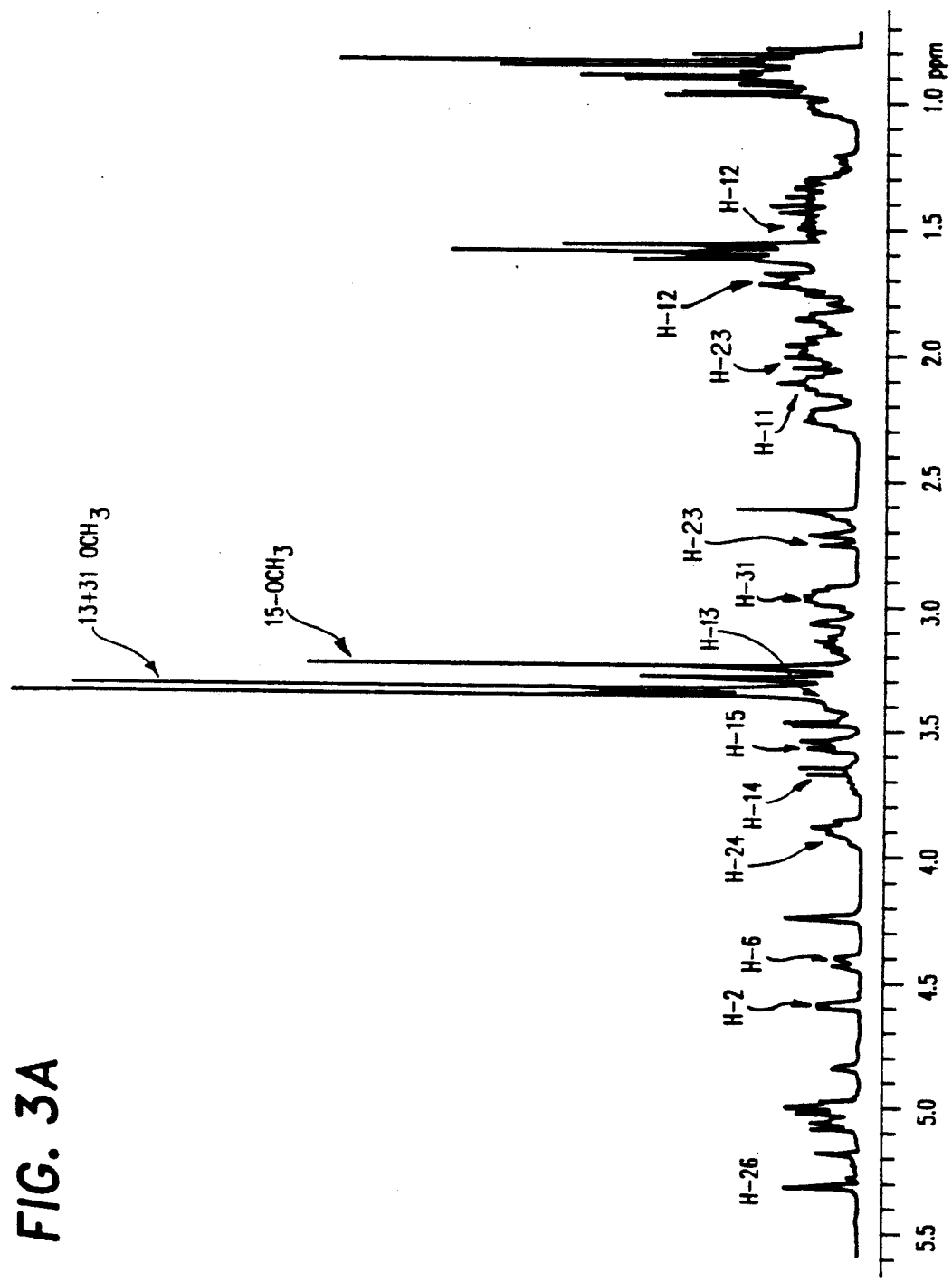
FIG. 3A is a $^1$H NMR spectrum taken at 400 MHz in CDCl$_3$ of FR-90052, also designated as "immunomycin
Figure 3B:
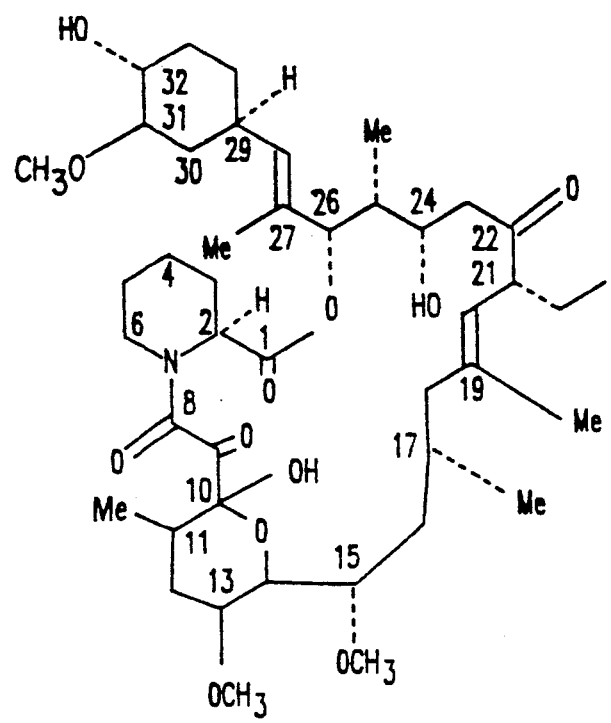
" and FIG. 3B illustrates its assigned molecular structure.

In addition there is provided a new FK-506 immunosuppressant, Compound II, which exhibits positive inhibition of T-cell activation by the T-cell proliferation assay and exhibits a proton nuclear magnetic resonance spectrum illustrated in FIG. 2 and has an assigned structure as also identified in FIG. 2.

Also provided is a pharmaceutical composition containing a therapeutically effective amount of Compound II in combination with a pharmaceutically acceptable, substantially non-toxic carriere or excipient.

In addition, there is provided a method of use for treating human host to prevent transplantation rejection, or for treating autoimmune disease or infectious disease comprising administering to said host a therapeutically effective amount of Compound I or II.

Furthermore there is provided a biologically pure culture of Streptomyces lavendulae, ATCC No. 55209.

DETAILED DESCRIPTION OF THE INVENTION AND PREFERRED EMBODIMENTS

The present invention involves the fermentation of *Streptomyces lavendulae*, ATCC No. 55209, together with FR-900520 to produce Compound I. The microorganism is currently on deposit under the terms of the Budapest Treaty with the American Type Culture Collection, 12301 Parklawn Dr. in Rockville, Md. as ATCC No. 55209. The microorganism is also maintained in The Merck Culture Collection as MA 6954. The physical characteristics and taxonomy, including morphological, cultural, biological and physiological characteristics are briefly described hereinbelow.

The following is a general description of *Streptomyces lavendulae* strain ATCC 55209 which transforms immunoregulant FR-900520 to Compound I. Observations of growth, general cultural characteristics and carbon source utilization were made in accordance with the methods of Shirling and Gottleib (Internat. J. System. Bacteriol. 16:313-340). Chemical composition of the cells was determined using the methods of Lechevalier and Lechevalier (in Actinomycete Taxonomy, A. Dietz and D. W. Thayer, Ed. Society for Industrial Microbiology, 1980). Coloration of the culture was determined by comparison with color standards contained in the Inter-Society Color Council-National Bureau of Standards Centroid Color Charts (U.S. Dept. of Commerce National Bureau of Standards Supplement to NBS Circular 553, 1985).

Source—This culture was isolated from a soil sample collected in Piscataway, N.J.

Analyst Wall Composition—Peptidoglycan contains LL-diaminopimelic acid.

General growth characteristics—Good growth on yeast malt extract agar (YME), inorganic salt starch agar, oatmeal, trypticase soy agar, and peptone iron agar. Moderate growth on glycerol asparagine agar. Sparse growth on Czapek's agar and tap water agar supplemented with NZ-amine (Shefield Chemical Co.) Culture also grows in tryptone yeast extract broth. Culture grows at 27° C. and 37° C.

Colony morphology—(on YME at 21 d) Substrate mycelium is slightly yellow brown. Aerial mycelium white. Spore mass is abundant and pinkish gray in color. Colonies are opaque, raised, with lobate edges, rubbery in texture with a rough surface texture.

Micromorphology—Aerial mycelia (0.76 μm) arise from substrate mycelia and are branched and slightly flexous. In mature cultures (7-28d p.i.) the aerial mycelium terminates in flexous chains of spores that occasionally terminate in hooks, loops or extended spirals. This characteristic is especially noticeable in areas of dense aerial development. Sporulation occurs on YME, inorganic salts-starch agar, gylcerol asparagine agar, tap water agar with NZ-amine and Czapek's agar.

Miscell physiological reactions Culture—produces $H_2S$ in peptone-iron agar. Melanoid pigments are formed in TY broth and on peptone iron agar slants. Starch is weakly hydrolyzed. Carbon source utilization pattern is as follows: moderate utilization of cellobiose, α-D-glucose, D-maltose, and D-mannose; poor utilization of D-fructose, α-D lactose, β-D-lactose; no utilization of D-arabinose, L-arabinose, inositol, D-mannitol, D-raffinose, L-rhamnose, sucrose, D-xylose, or L-xylose.

Diaznosis—Cell wall analysis reveals that ATCC #55209 has a type I cell wall. Morphological studies reveal that the culture produces long chains of spores on flexous sporophores that occasionally terminate in loops, hooks, or extended spirals. Sporophores arise from the aerial mycelium. These are characteristics typical for strains of Streptomyces.

A comparison of the phenotypic data of ATCC No. 55209 with that of the validly published species of Streptomyces in the taxonomic literature (following References 1-7) shows that this strain strongly resembles *Streptomyces lavendulae*, *Streptomyces virziniae*, *Streptomyces flavotricini*, *Streptomyces goshikiensis*, and *Streptomyces colombiensis*. These species fall into either the gray or red series and characteristically produce spores on flexous sporophores that terminate in loops, hooks or spirals. Most produce melanoid pigments and all essentially exhibit identical carbon source utilization patterns. *Streptomyces virginiae*, *Streptomyces flavotricini*, *Streptomyces goshkiensis*, and *Streptomyces colombiensis* are currently considered to be subjective synonyms of *Streptomyces lavendulae* (7). Based upon these results, ATCC No. 52209 is considered to be a novel strain of *Streptomyces lavendulae*.

Literature References

1. Shirling, E. B. and Gottlieb, D., Int. J. System Bacteriol.18:69 (1968)
2. Shirling, E. B. and Gottlieb, D., Int. J. System, Bacteriol.18:279 (1968)
3. Shirling, E. B. and Gottlieb, D., Int. J. System, Bacteriol.19:391 (1969)
4. Shirling, E. B. and Gottlieb, D., Int. J. System, Bacteriol.22:265 (1972)
5. Nonomura, H. J., Ferment. Technol.52:78 (1974)
6. Pridham, T. and Tresner, H., in Bergey's Manual of Determinative Bacteriology, Eighth Edition, R. E. Buchanan and N. E. Gibbons, Ed., Williams and Wilkins, Baltimore (1974)
7. Loci, R. in Bergy's Manual of Systematic Bacteriology, Vol.4., St. Williams, M. E. Sharpe and J. G. Holt. Ed., Williams and Wilkins, Baltimore. (1989)

| Carbohydrate utilization patterns of ATCC 55209 at 21 day ||
| --- | --- |
| Carbon source | Utilization by ATCC 55209 |
| D-arabinose | 0 |
| L-arabinose | 0 |
| cellobiose | 2 |
| D-fructose | 1 |
| inositol | 0 |
| α-D-lactose | 1 |
| β-D-lactose | 1 |
| D-maltose | 2 |
| D-mannitol | 0 |
| D-mannose | 2 |
| D-raffinose | 0 |
| L-rhamnose | 0 |
| sucrose | 0 |
| D-xylose | 0 |
| L-xylose | 0 |
| a-D-glucose (control) | 2 |

3 = good utilization,
2 = moderate utilization,
1 = poor utilization,
0 = no utilization

| Cultural characteristics of ATCC 55209 at 21 days | | | | |
|---|---|---|---|---|
| Medium | Amount of Growth ATCC 55029 | Aerial Mycelium ATCC 55029 | Soluble Pigments | Reverse Color |
| Yeast Extract Malt Extract | Good | Aerial mycelium pinkish gray (10 pk Gray). Spores borne in slightly flexous chains with terminal hooks and loops. | none noted | Slight yellow brown (74 s. yBr) |
| Glucose Asparagine | Moderate | Aerial mycelium pinkish gray (10) pk Gray). Spores borne in slightly flexous chains with occasional hooks and loops. | none noted | Yellow white (92 y. White) |
| Inorganic Salts Starch | Good | Aerial mycelium pinkish gray (10) pk Gray). Spores borne in slightly flexous chains with numerous hooks and loops. Starch weakly hydrolyzed. | none noted | Yellow white (92 y. White) |
| Oatmeal | Good | Aerial mycelium pinkish gray (10) pk Gray). Spores borne in slightly flexous chains with hooks and loops. Starch weakly hydrolyzed. | none noted | Yellow white (92 y. White) |
| Tap Water | Sparse | Yellow white (92 y, White). Spores borne in slightly flexous chains with hooks, loops and spirals. | none noted | Yellow white (92 y. White) |
| Czpak | Sparse | Yellow white (92 y, White). Flexous aerial mycelium. | none noted | Yellow white (92 y, White) |
| Peptone Iron | Good | — | Melanin positive, H₂S positive. | — |

The present invention process can be practiced with any Compound I producing strain of *Streptomyces lavendulae*, and particularly preferred is the ATCC No. 55209 strain.

In general, Compound I can be produced by culturing (fermentation) of the Actinomycete strain, in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, raffinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, polypropylene glycol, mineral oil or silicone may be added.

The FR-900520 (also referred to as "FK-520" by Merck) starting material can be obtained by the fermentation of *S. hygroscopicus* var. *ascomyceticus*, ATCC No. 14891, as described in U.S. Pat. No. 3,244,592, and by the fermentation of *S. hygroscopicus* subsp. *yakushimaensis* No. 7278, to produce FR-900520, as described in EPO Publication No. 0184162 to Fujisawa, and U.S. Pat. No. 4,894,366.

As to the conditions for the production of Compound I in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of Compound I. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of Compound I and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 10 hours to 20 hours, which may be varied according to fermentation conditions and scales. Preferably, the production cultures are incubated for about 17 hours at 27° C. on a rotary shaker operating at 220 rpm, wherein the pH of the fermentation medium is maintained at 7.0 to harvest.

Preferred culturing/production media for carrying out the fermentation include the following media:

| Seed Medium | g/liter |
| --- | --- |
| Dextrose | 1.0 |
| Dextrin | 10.0 |
| Beef Extract | 3.0 |
| Ardamine pH | 5.0 |
| NZ Amine Type E | 5.0 |
| $MgSO_4.7H_2O$ | 0.05 |
| $K_2HPO_4$ | 0.37 |
| Adjust pH to 7.1 | |
| Add $CaCO_3$ 0.5 g/l | |

| Transformation Medium B | g/liter |
| --- | --- |
| Glucose | 20 |
| Soya Meal | 5 |
| Yeast Autolysate | 5 |
| NaCl | 5 |
| MES | 9.8 |
| Adjust pH to 7.0 | |

The produced Compound I can be recovered from the culture medium by conventional means which are commonly used for the recovery of other known biologically active substances. The Compound I substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

The product Compound I from the fermentation exhibits antagonist activity versus the FK-506 immunosuppressive activity by the "T-cell proliferation assay" and possesses utility on this basis and exhibits the following physical characteristics:

1. White amorphous powder
2. Solubility in methanol
3. Molecular weight of 793, as determined by FAB mass spectroscopy (observed M+Li=800), is consistent with the assigned structure in FIG. 1.

The Compound I obtained according to the fermentation processes as explained above can be isolated and purified in a conventional manner, for example, extraction, precipitation, fractional crystallization, recrystallization, chromatography, and the like.

It is to be noted that in the aforementioned fermentation reactions and the post-treatment of the fermentation mixture therein, the conformer and/or stereo isomer(s) of Compound I due to asymmetric carbon atom(s) or double bond(s) of the Compound I may occasionally be transformed into the other conformer and/or stereoisomer(s), and such cases are also included within the scope of the present invention.

Also described is a new enzyme, 31-O-desmethyl-immunomycin O-methyltransferase (DIMT) which can specifically and preferentially methylate the C-31 hydroxy group in Compound I to produce Compound II.

The enzyme can be extracted out of the microorganism Streptomyces hygroscopicus var. ascomyceticus, ATCC No. 55087. Employing the enzyme in its active form, supplemented with $Mg^{+2}$ ion, in the presence of the methyl donor, S-adenosyl methionine (SAM), Compound I can be C-31 methylated to produce Compound II.

The enzyme described can be used as a cell free or purified enzyme. Purified DIMT has a molecular weight of about 32 K daltons, as measured by SDS-PAGE, an isoelectric point (PI) of 4.4, and capable of catalyzing the C-31 O-methylaion of a C-31 hydroxy containing FK-506 type molecule, in the presence of a methyl transfer agent, when supplemented with $Mg^{+2}$ ion.

The enzyme can be isolated from the microorganism, Streptomyces hygroscopicus var. ascomyceticus, ATCC No. 55087 and purified for enzymatic use by the procedure described in the Examples.

The enzyme is useful in a process for methylating the C-31 hydroxy group in Compound I involving the step of contacting Compound I with the methyl transfer agent, e.g., S-adenosyl methionine, in the presence of the DIMT enzyme described, supplemented with $Mg^{+2}$ ion, in an aqueous solvent therefor.

Generally, the process is conducted at a pH from about 7-9 and in the temperature range of about 25°-40° C.

The aqueous solvent system is generally a phosphate buffer of about pH=7-8.

The $Mg^{+2}$ ion is supplied as a soluble magnesium salt, e.g., magnesium chloride, magnesium sulfate, magnesium citrate, and the like.

Isolation and purification of Compound II can be accomplished by conventional techniques including HPLC or reverse phase HPLC as described in the examples.

The enzyme is specific in methylating only the C-31 hydroxy group in Compound I.

Structures of the compounds involved in this invention include the following:

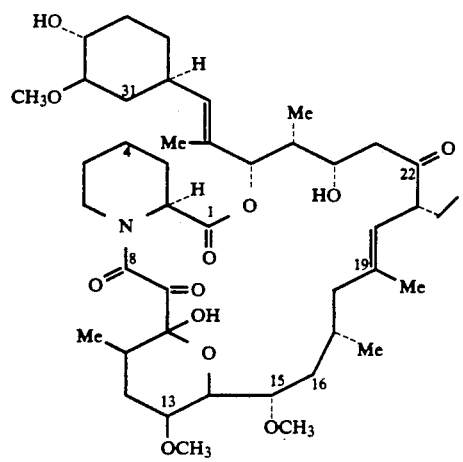

FR-900520
FK-520
Immunomycin

Compound I

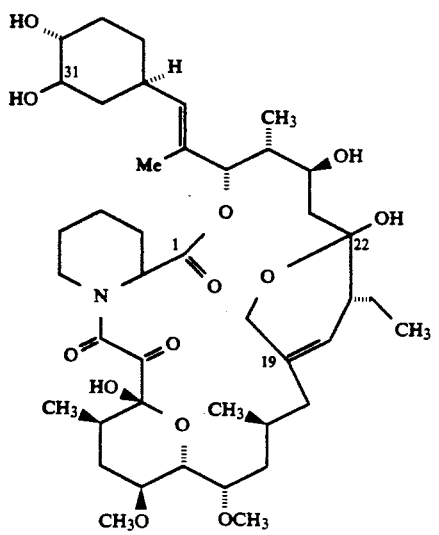

Compound II

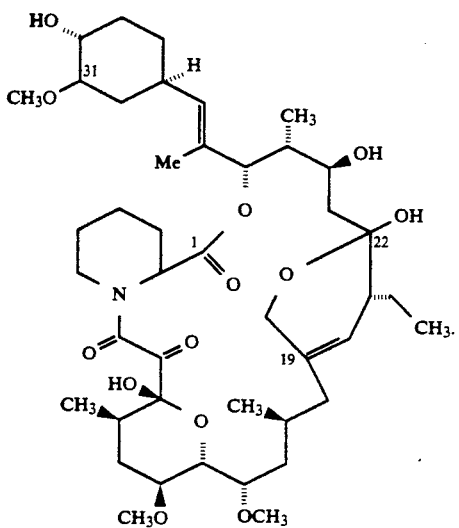

The FR-900520 immunosuppressant is disclosed by Fujisawa in EPO 0184162, having a slightly different numbering system than Merck, i.e.

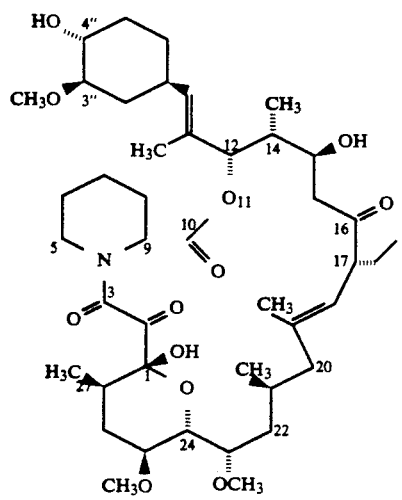

with the assigned chemical name; 17-Ethyl-1,14-dihydroxy-12-[2-(4-hydroxy-3-methoxycyclohexyl)-1-methylvinyl]-23-25-dimethoxy-13,19,21,27-tetramethyl-11,28-dioxa-4-azatricyclo [22.3.1.0$^{4,9}$]octacos-18-ene-2,3,10,16-tetraone.

The Compounds I and II of the present invention possess immunosuppressant pharmacological activity therefore are useful in a therapeutic program involving FK-506 type therapy designed for the treatment and prevention of the transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosus, Hashimoto's thyroiditis, multiple sclerosis, myasthenia gravis, type I diabetes, uveitis, and the like.

The pharmaceutical compositions of this invention can be used in the form of a pharmaceutical preparation, for example, in solid, semisolid or liquid form, which contain the Compounds I or II, of the present invention, as an active ingredient, in admixture with an organic or inorganic carrier orexcipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to a human, it is preferable to apply it by parenteral or enteral administration. While the dosage of therapeutically effective amount of the Compound I or II, varies from, and also depends upon the age and condition of each individual patient to be treated, a daily dose (calculated on the basis of a 70 kg man) of about 0.01–1000 mg, preferably 0.1–500 mg and more preferably 0.5–100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples are given for the purpose of illustrating the present invention and should not be construed as being limitations on the scope or spirit of the instant invention.

EXAMPLE 1

Microorganism and Culture Conditions

A frozen vial of culture, ATCC No. 55209, was used to inoculate a 250 ml baffled shake flask containing 50 ml of an autoclaved (sterilized) seed medium consisting of (in units of grams/liter) dextrin 10.0, dextrose 1.0, beef extract 3.0, ardamine PH (Yeast Products, Inc.) 5.0, N-Z Amine type E 5.0, MgSO$_4$.7H$_2$O 0.05, KH$_2$PO$_4$ 0.37, and CaCO$_3$ 0.5. The pH of the seed medium was adjusted to 7.1 before autoclaving. The seed was incubated in the seed medium at 27° C. for 24 hours on a rotary shaker operating at 220 rpm. A 2.5 ml aliquot of the resulting seed medium was used to inoculate a 250 ml non-baffled shake flask containing 50 ml of the following previously autoclaved (sterilized) fermentation medium:

| Soy-Glucose Medium | |
|---|---|
| Glucose | 20.0 |
| Soya Meal | 5.0 |
| Yeast Autolysate | 5.0 |
| NaCl | 5.0 |
| MES | 9.8 |
| Adjust pH to 7.0 | |

FR-900520 was added as a solution in dimethylsulfoxide to achieve a final concentration of 0.05 mg/ml concentration. The shake flask contents were subsequently incubated for 48 hrs. at 27° C. on a rotary shaker operating at 220 rpm.

Isolation and Purification

The whole broth (250 ml) was extracted three times with methylene chloride (3×250 ml). Methylene chloride extracts were combined, dried over sodium sulfate, and concentrated under vacuum to an oily residue. The residue was dissolved in methanol and subjected to high performance liquid chromatography (HPLC). HPLC was carried out on Whatman Magnum 20 Partisil 10 ODS-3 Column (22.1 mm ID×25 cm) at room temperature and monitored at 205 nm. The column was developed at 7 ml/min with a 65 minutes linear gradient from 35% to 80% acetonitrile in 0.1% phosphoric acid. The compounds were collected during repeated injections of the above described extract. The fraction with a retention time of 57 minutes (Compound I) was pooled, adjusted to pH 4.0, evaporated to remove acetonitrile, and desalted using a C18 Sep Pak (Waters Associate) to yield 4 mg of Compound I.

ANALYTICAL SPECTRAL DATA

Mass spectral data of the subject Compound I biotransformation product obtained by the incubation of FR-900520 with culture ATCC #55209, coupled with the NMR data, as shown in the spectrum of FIG. 1, is consistent with the following assigned molecular structured (I), also shown in FIG. 1 and illustrates the C-31 desmethyl and C-19/C-22 cyclic hemiketal characteristics in the structure:

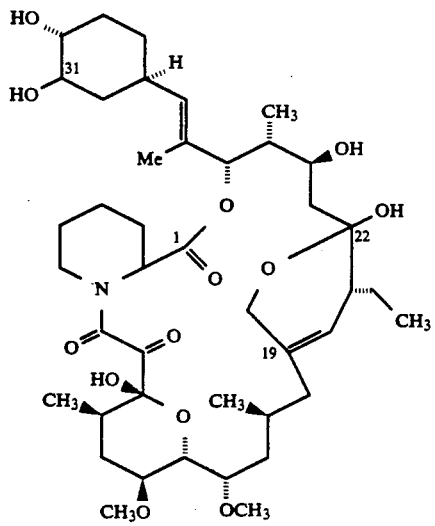

Key features of the NMR analysis of the above biotransformation product which are consistent with the 31-desmethyl cyclized structure (I) are given by the following points:
1. Loss of methoxy assigned to the 31-OCH$_3$ based on the downfield shift of H-31;
2. Absence of the 19-methyl;
3. Presence of a novel CH$_2$O (3.74 ppm and 4.06 ppm, Jgem:16 Hz) reasonably assigned to a derivatized 19-methyl;
4. Absence of typical 23-methylene signals;
5. Upfield shifted H-21;
6. A 0.6 ppm downfield displacement of H-20 and reduction of its vicinal coupling constant from 9 to approximately 7 Hz.

Reduction of the 22 ketone is implied by the above points 4 and 5. While the proton NMR spectrum did not allow a decision between a 19-CH20H and a 19-CH20R, the perturbations of H-20 (point 6) were suggestive of a cyclic structure. Based on a consideration of several possiblitites, I, is entirely consistent with both NMR and MS observations (i.e., the increase of two mass units is accounted for by the loss of methoxyl and the incorporation of oxygen).

EXAMPLE 2

Isolation and characterization of
S-adenosyl-L-methionine:
31-O-desmethylimmunomycin O-methyl-transferase Immunomycin (See Structure, supra) is a new macrocylic lactone/lactam antibiotic with effective immunosuppressive and antifungal activities (See EP Publication No. 0323865 (1989) by F. J. Dumont, et al.). Precursor feeding studies in this laboratory has established the polyketide nature of the macrocyclic structure. Furthermore, the data from the feeding studies indicate that the three methyl groups at positions 13, 15 and 31 originate from methionine through S-adenosyl-L-methionine (SAM). With the development of a mutant strain of S. hygroscopicus var. ascomyceticus (MA 6674) which produces 31-O-desmeihylimmunonycin, it has become possible to isolate and characterize the enzyme, S-adenosyl-L-methionine: 31-O-desmethylimmunomycin O-methyltransferase (DIMT).

Bacterial Growth and Mycelium Preparation

Frozen vegetative mycelium of *Streptomyces hygroscoipicus* var. *ascomyceticus* (ATCC 55087) was cultured in the seed and fermentation media. Mycelial cells were harvested at 72 hours and washed three times with 50mm phosphate buffer, pH 7.5, containing 0.5M KCl and finally with the same buffer with no KCl. Washed mycelium was used for the preparation of the cell-free extract.

Time Course of the Mycelial Growth and Immunomycin Production

At different time intervals, an aliquot of the fermentation culture was centrifuged at 2000 rpm for 10 minutes and packed cell volume was determined. Similarly, an aliquot was extracted with methanol and immunomycin production was quantitated by HPLC.

S-adenosyl-L-methionine: 31-O-desmethylimmunomycin O-methyltransferase (DIMT) Assay and Product Identification The assay was carried out in 1 ml. mixture containing 0.025 mM 31-desmethylimmunomycin, 1 mM MgSO$_4$ and different quantities of the enzyme source in 50 mM phosphate buffer, pH 7.5. Reaction was initiated by the addition of 1 nmole of $^{14}$C-SAM (S-adenosyl-L-[methyl-$^{14}$C] methionine with the specific activity of 46 mCi/mmole. Incubation of the complete mixture was carried out at 34° C. for 20 minutes and the reaction was terminated by the addition of ethyl acetate. Product of the reaction was extracted with 2 ml of ethyl acetate and 1 ml of the extract was used for TLC and HPLC analysis. For the analysis of the radioactive reaction product (immunomycin), the ethyl acetate extract was spiked with the standard immunomycin and subjected to the TLC with a plate having plastic support. The plastic sheet was developed in chloroform:methanol (9:1) and area showing standard immunomycin under UV-light was cut and the radioactivity in the cut-strip was measured. The amount of the product formed was calculated from the measured radioactivity. For the HPLC analysis of the product of the enzyme reaction, several enzymatic reaction mixtures were pooled and the extract was subjected to the TLC analysis as above. The area on the silica gel plate showing the band having an Rf value identical with the standard immunomycin was scraped and eluted with ethyl acetate. The ethyl acetate extract was washed with water, dried under nitrogen and the residue was subjected to the HPLC analysis on Partisil 5-ODS-3 column with acetonitrile:water:phosphoric acid (65:35:0.1) as the eluting solvent. One milliliter fractions were collected and a portion of each fraction was examined for the radioactivity.

Isolation of the 31-O-methyltransferase (DIMT)

(All of the procedures were carried out at 4° C. in the cold room or on ice). Washed mycelium was suspended in 50 mM phosphate buffer, pH 7.5 containing 1 mM PMSF and 1 mg/ml of lysozyme. The resulting suspension was stirred overnight and centrifuged at 15000 rpm for 30 minutes. The pellet thus obtained was sonicated for 2' at 30" intervals by microtip-equipped sonifier. The cell homogenate was centrifuged as before and the supernatants were combined and re-centrifuged at 105K × g for 45 minutes. The supernatant was then brought to 1% streptomycin sulfate, stirred for 30 minutes and centrifruged at 105K × g as before. The resulting supernatant, designated as the crude extract, was made to contain 0.1 mM S-adenosyl-L-methionine (SAM) and 10% ethanol following the buffer system suggested for the isolation of the methyltransferases from *Strepomyces fradiae*, a tylosin-producing organism (See N. J. Bauern, et al., *J.B.C.* Vol. 263, D. 15619 (1988).) The crude extract was then brought to 30% ammonium sulfate saturation and after 30 minutes stirring was centrifuged at 15000 rpm for 30 minutes. The resulting supernatant was brought to 60% ammonium sulfate saturation and after identical stirring and centrifugation procedures, its precipitate was recovered. This fraction, designated as 30–60% cut, was dialyzed against 50 mM phosphate buffer, pH 7.5, containing 1 mM PMSF, 0.1 mM SAM and 10% ethanol (Buffer L) using PD-10 Pharmacia column. This fraction was chromatographed on a DEAE-Sepharose containing column. This column was eluted stepwise with buffer L containing various concentrations of KCl. The DIMT activity was completely eluted with the buffer containing 0.3M KCl. The DIMT active fraction was dialyzed against buffer L and applied on the preparative MonoQ HR10/10-FPLC column previously equilibrated with the same buffer. One milliliter fractions, eluted under a linear gradient from zero to 1M KCl with a 130 minute duration in buffer L with a flow rate of 60 ml/hr, were collected and examined for the DIMT activity. Fractions, showing the DIMT activity were pooled and after the necessary treatment was subjected to an analytical MonoQ HR5/5-FPLC column. This column was developed as above except for the KCl concentration which was 0.5M KCl and fractions were examined for the DIMT activity. The active fractions were pooled, and subjected to chromatofocusing. Chromatofocusing was carried out on Pharmacia FPLC system. Column was developed with the polybuffer and 1 ml fractions with a flow rate of 30 ml an hour were collected. The pH of the fractions was adjusted to 7.2 immediately after elution and pH determination. Enzyme assay was carried out on various fractions and peak DIMT activity was located in fraction 35. This fraction was then applied on a Superose-12 column. This column was eluted with buffer L containing 150 mM NaCl with a flow rate of 18 ml/hr. and 0.3 ml fractions were collected. The fraction having the peak DIMT activity was finally subjected to a 12.5% native polyacrylamide electrophoresis (native-PAGE). After electrophoresis, cuts were made across the face of the gel and each gel cut was eluted by diffusion and assayed for the DIMT activity. The DIMT activity was located in the fraction eluted from the gel cut with Rf value higher than Rf value of the standard egg albumin in the same gel.

General Properties of DIMT

Examination of the optimal temperature, pH and metal requirement of the DIMT activity was carried out on the enzyme preparation obtained from DEAE-Sepharose column. For kinetic analysis, a preparation which had been purified through a second MonoQ column chromatography was utilized.

Molecular Weight and Isoelectric Point Determination of DIMT

The molecular weight of the native enzyme was determined by gel filteration chromatography on Superose-12 column. Column was equilibrated and run in buffer L containing 150 Mm NaCl and with a flow rate of 18 ml/hour. The apparant molecular weight of the denatured enzyme was estimated by SDS-PAGE according to Laemmli (*Nature* (London) Vol. 227, pp. 680–685 (1970)). In both gel filteration and SDS-PAGE, bovine serum albumin (Mr=66000), egg albumin (Mr=45000), and carbonic anhydrase (Mr=31000), and cytochrome C (Mr=12400) were used as standards. Isolectric point of the purified enzyme was estimated by both chromatofocusing on a Pharmacia MonoP HR5/20 column with a pH interval of 7-4 and calibrated isoelectric focusing-PAGE having interval of 3-9.

General Analytical Methods

Native-PAGE was carried out according to Laemmli, supra, with the elimination of the SDS from the buffer system. Protein concentration was determined by the Bio-Rad assay system with bovine serum albumin as standard.

Time Course of the Mycelial Growth and Immunomycin Production

Packed cell volume and immunomycin production, as a function of time, were determined as an indicator for the titer of the immunomycin biosynthetic enzymes. Both the mycelial mass and immunomycin production peaked between 72 to 95 hours into the age of the cultures. It was therefore decided to use 72 hour old mycelium for the isolation of the DIMT enzyme.

Properties and Localization of DIMT

Initially, using the crude extract, enzyme assay was established based on the assay system previously reported for the S-adenosyl-L-methionine-dependent methylation of tylosin and avermectin (See Bauern, N. J. et al., *J. Biol. Chem.* 263, p. 15619 (1988) and Schulman, M. D. et al., *Antimicrobial Agents Chemotherapeutics*, 29, p. 620 (1989)). This preparation showed an absolute requirements for SAM and magnesium ions and EDTA completely inhibited the activity. The enzyme activity was also inhibited by ammonium sulfate, which was reversed after complete dialysis. Optimal reaction temperature and pH were also established to be 35° C. abd 8.5, respectively. Using the optimal condition, the enzyme activity could only be detected in the cell-free extract (crude extract) obtained after the 105K× g centrifugation step. No enhancement of the activity was observed upon reconstitution of the pellet with the crude extract.

Isolation and Purification of DIMT

Using optimized assay condition, a 72-hour old mycelial cells provided us with a cell-free preparation which was functional with regard to DIMT activity. The fraction containing this activity was isolated to a high degree of purity after a series of purification steps which included ammonium sulfate precipitation, DEAE-Sepharose, preparative and analytical MonoQ, chromatofocusing and Superose-12 column chromatographies. The elution profiles and DIMT activity of the fractions from preparative MonoQ, analytical MonoQ, chromofocusing P and Superose-12 columns were determined. The DIMT was consistently eluted in a single peak with increasing specific activity. High degree of purity of the DIMT was finally achieved when a highly purified fraction from Superose-12 column was subjected to native-PAGE. Fraction which was eluted from the native polyacryl-amide gel after electrophoresis was enzymatically active and showed a single band on SDS PAGE and isoelectric focusing gel.

Molecular Weight and Isoelectric Focusing Point

Molecular weight of the purified DIMT was determined by SDS-PAGE and Superose-12 column chromatography. From the calibrated SDS-PAGE the purified DIMT showed a single homogeneous band with an apparant molecular weight of about 32,000. This preparation was also symmetrically eluted from a calibrated Superose-12 column with an elution volume identical to that of a standard carbonic anhydrase (MR=31000), therefore indicating an apparent molecular weight of 31000 for the native enzyme. Isoelectric point of the purified DIMT was estimated by both chromatofocusing and calibrated isoelectric focusing-PAGE. Both systems demonstrated an isoelectric point of 4.4 for the native enzyme.

S-adenosyl-L-methionine (SAM) Dependency and Magnesium Ion Requirement

DIMT requires SAM and $Mg^{+2}$ for activity. As found, there is also major inhibition of DIMT activity by EDTA, sinefungin and S-adenosyl-homocysteine (SAH), reconfirming the SAM and $Mg^{+2}$ requirement for this enzyme.

pH and Temperature Dependencies of DIMT

The optimum activity of DIMT was seen at pH 8.5 and a temperature of 35° C.

Kinetic studies. With the established incubation conditions, the enzymic velocity was directly proportional to the amount of protein up to about 60 ug. Under similar condition, when 25 ug of the protein was incubated for different period of time, the initial velocity was maintained for 30 minutes. Under the condition for measurement of the initial velocity, the apparent Km and Vmax of DIMT were determined with 40 uM SAM, while the kinetic utilization of SAM was examined with 25 umM of 31-O-desmethylimmunomycin as cosubstrate. The apparent Km and Vmax of DIMT for 31-O-desmethylimmunomycin and SAM were determined from the Lineweaver-Burk reciprocal plots. The graphically obtained kinetic parameters indicate values of 45.5 runole/hr/mg and 11 uM for apparent Vmax and Km, respectively, when 31-O-desmethylimmunomycin was the variable substrate. Similarly, values of 100 nmole/hr/mg and 12.5 uM were estimated for Vmax and Km when SAM was utilized as the variable substrate.

EXAMPLE 3

General Procedure for Large-scale enzyme assay

The reaction mixture contained 35 mg of a partially purified DIMT fraction; 2 mM of magnesium sulfate; 6.25 uM substrate; 60 uM SAM in a total volume of 10 ml which was adjusted with 50 mM of phosphate buffer, pH=7.30. The reaction was intiated by the addition of SAM under incubation conditions as previously reported. The reaction mixture was extracted with ethylacetate and, after work-up, was subjected to a TLC system in which chloroform:methanol (9:1) was used as solvent. The silica gel from the area of the TLC plate, having Rf value that was established from the isolation of radioactivity in a corresponding experiment in which 14-C SAM had been used, was scraped off and eluted extensively with ethylacetate. Ethylacetate extract was then prepared for purification by reverse-phase HPLC. Reverse-phase HPLC system was carried out in a solvent system consisting of water:acetonitrile:-phosphoric acid (45:55:0.1) at 60° C. Fractions eluting with an elution time corresponding to what had already been established for the product of the enzymic assay in which 14-C SAM had been used were collected and pooled. Pooled fractions were then further purified for biological testing and chemical characterization.

Enzymatic Synthesis of the Compound II

Compound I was directly used in our radioisotope-based assay system as it was supplied. The retention time of this material was 19.44 minutes in our reverse phased HPLC system. The product of the enzymatic reaction in which this material and [$^3$H-CH$_3$]-SAM (S-adenosyl-L-methionine) had been used as substrate/co-substrate was isolated and examined by the radio-TLC and radio-HPLC systems. In our radio-TLC, a radioactive fraction with characteristic Rf was detected which was suggestive of methylation of the substrate. On the radio-HPLC system the radioactivity was eluted with fractions 25-27 with the peak elution of the radioactivity in fraction 26. Based on the informations obtained from the radio-TLC and radio-HPLC, a large scale enzymatic reaction was carried out and the product of the reaction was isolated and examined by HPLC. The elution profile of this material with the peak elution time at 25.15 minutes corresponding to fraction 26, similar to the elution position of the radioactive fraction. The elution time of this enzymatically produced material is about four minutes shorter than the elution time (31.79 minutes) of the standard immunomycin in an identical HPLC system, indicating distinct nature of this enzymatically produced compound. This material was therefore isolated and submitted for FAB and NMR spectroscopic analysis. The result of FAB spectroscopy indicated the addition of 14 atomic mass units [814−7(Li)=807] as a result of enzymatic methylation and the NMR was characteristic (FIG. 2).

Biological Activity

HPLC purified samples of Compound I, Compound II and FR-900520 were evaluated for biological activity in the same set of experiments. The results of these experiments indicated an IC$_{50}$ of about 11, 6, and 1 nM for these compounds, respectively.

EXAMPLE 4

T-Cell Proliferation Assay

1. Sample Preparation

Purified Compound I, as prepared by HPLC above, was dissolved in absolute ethanol at 1 mg/ml.

2. Assay

Spleens from C57B1/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 Mm glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The control, being the medium without test drug, and various below-indicated dilutions of the sample (above-described purified Compound I) to be tested were then added in triplicate wells at 20 μl/well. FR-900506 was used as a standard. The culture plates were then incubated at 37° C. in a humidified atmosphere of 5% CO$_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as percent inhibition of tritiated thymidine uptake (proliferation) as follows:

$$\% \text{ Inhibition} = 100 - \left[ \frac{\text{Mean cpm sample tested}}{\text{Mean cpm control medium}} \times 100 \right]$$

The results of % inhibition at various concentrations of Compound I are presented in the following Table:

TABLE

Effects of Compound I on the proliferative response of Splenic T-cells stimulated with ionomycin + PMA

| Sample | Concentration (nM) | Percent of Inhibition |
|---|---|---|
| | 315.2 | 98 |
| | 157.6 | 98 |
| | 78.8 | 95 |
| | 39.4 | 89 |
| | 19.7 | 65 |
| | 9.9 | 39 |
| | 4.9 | 0 |
| | 2.5 | 0 |

Notes:
1. Mouse T cell cultures were pulsed with $^3$H thymidine for 4 hours prior to harvesting at 48 hours.
2. Standard FR-900506 (10 ng/ml) gave 99% inhibition.
3. IC$_{50}$ = 11.5 ng/ml = 14.5 nM, for Compound I, and generally in the range of 10 to 18 × 10$^{-9}$ molar.
4. Inhibition of T-Cell proliferation by Compound I was reversed by the addition of 50 units/ml of IL-2 (recombinant IL-2) at the initiation of culture.
5. Compound II also gave positive results in the above described T-cell proliferation assay.

What is claimed is:

1. An immunosuppressant compound having the structure:

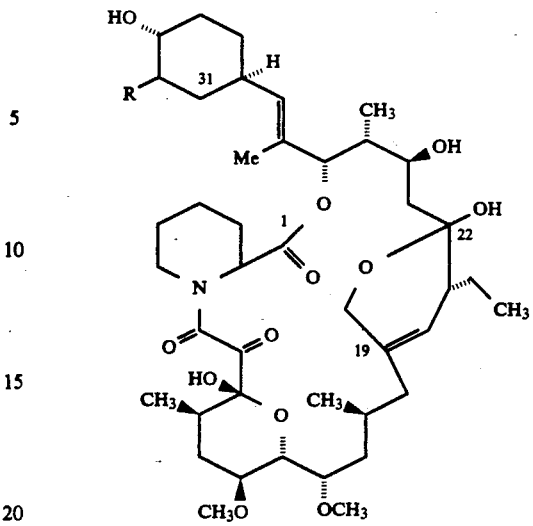
wherein R is OH or CH3O.
2. A pharmaceutical composition useful for preventing transplantation rejection comprising a therapeutically effective amount of a compound of claim 1 in combination with a pharmaceutically acceptable, substantially non-toxic carrier or excipient.
* * * * *